US006955655B2

(12) United States Patent
Burbank et al.

(10) Patent No.: US 6,955,655 B2
(45) Date of Patent: Oct. 18, 2005

(54) HEMOFILTRATION SYSTEM (75) Inventors: Jeffrey H. Burbank, Boxford, MA (US); Charles D. Finch, Jr., Clinton, MS (US); James M. Brugger, Newburyport, MA (US)

(73) Assignee: NxStage Medical, Inc., Lawrence, MA (US)

( * ) Notice: Subject to any disclaimer, the term of this patent is extended or adjusted under 35 U.S.C. 154(b) by 235 days.

(21) Appl. No.: 09/894,236

(22) Filed: Jun. 27, 2001

(65) Prior Publication Data
US 2001/0037079 A1 Nov. 1, 2001

Related U.S. Application Data (62) Division of application No. 08/800,881, filed on Feb. 14, 1997, now abandoned.

(51) Int. Cl.[7] .................. A61M 37/00; B01D 11/00; B01D 35/00; B01D 63/00; C02F 1/44
(52) U.S. Cl. ............... 604/5.01; 604/6.09; 604/6.11; 604/6.16; 210/646; 210/650; 210/195.2; 210/321.72; 210/87; 210/257.2
(58) Field of Search .............. 422/44–8; 604/4.01, 604/6.01, 5.01–5.04, 6.09, 6.11, 6.16; 210/321.71–321.72, 210/321.6, 767, 646–47, 650–52, 194, 195.1–195.2, 210/348, 416.1, 500.1, 500.21, 252, 257.1, 210/257.2, 258–262, 85–90, 97, 98, 103, 210/104, 109, 110, 143; 128/DIG. 3, 898

(56) References Cited

U.S. PATENT DOCUMENTS

| 3,774,762 A | 11/1973 | Lichtenstein |
| 3,912,455 A | 10/1975 | Lichtenstein |
| 4,108,574 A | 8/1978 | Bartley et al. |
| 4,127,481 A | 11/1978 | Malchesky |
| 4,468,329 A | 8/1984 | Shaldon |
| 4,479,760 A | 10/1984 | Bilstad |
| 4,479,761 A | 10/1984 | Bilstad |
| 4,479,762 A | 10/1984 | Bilstad |
| 4,514,295 A | 4/1985 | Mathieu |
| 4,661,246 A * | 4/1987 | Ash .................. 210/87 |
| 4,670,007 A | 6/1987 | Wheeldon et al. |
| 4,702,829 A | 10/1987 | Polaschegg |
| 4,711,715 A | 12/1987 | Polaschegg |
| 4,713,171 A | 12/1987 | Polaschegg |
| 4,892,518 A | 1/1990 | Cupp |

(Continued)

FOREIGN PATENT DOCUMENTS

FR 2684897 6/1993

(Continued)

OTHER PUBLICATIONS

Canaud et al., "Failure of a daily haemofiltration programme using a highly permeable membrane to return $\beta_2$-microglobulin concentrations to normal in haemodialysis patients," Nephrol. Dial. Transplant 7:924-930 (1992).

(Continued)

Primary Examiner—Patricia Bianco
(74) Attorney, Agent, or Firm—Proskauer Rose LLP (57) ABSTRACT A hemofiltration system and method is provided that allows for high flow rate, accurate determination of net fluid withdrawal from or addition to a patient, and simple and reliable home operation. A removable, disposable assembly includes a filter housing and pump member including one or more fluid conduits mounted against the pump member. When the disposable filter/pump member assembly is attached to the treatment system, a pump roller mechanism associated with the system actuates the conduits mounted against the pump member. A disposable waste receptacle and fluid replacement (infusate) reservoir can be provided as an integral part of the disposable filter/pump member assembly.

15 Claims, 7 Drawing Sheets

U.S. PATENT DOCUMENTS

| | | |
|---|---|---|
| 4,894,150 A | 1/1990 | Schurek |
| 4,923,598 A | 5/1990 | Schal |
| 4,997,570 A | 3/1991 | Polaschegg |
| 5,041,098 A * | 8/1991 | Loiterman et al. .......... 604/175 |
| 5,204,681 A | 4/1993 | Greene |
| 5,211,849 A * | 5/1993 | Kitaevich et al. .......... 604/5.04 |
| 5,230,702 A | 7/1993 | Lindsay |
| 5,291,205 A | 3/1994 | Greene |
| 5,330,448 A | 7/1994 | Chu |
| 5,344,568 A | 9/1994 | Kitaevich |
| 5,441,636 A | 8/1995 | Chevallet |
| 5,484,397 A | 1/1996 | Twardowski |
| 5,522,998 A | 6/1996 | Polaschegg |
| 5,533,957 A | 7/1996 | Aldea |
| 5,536,412 A * | 7/1996 | Ash .......................... 210/645 |
| 5,581,257 A | 12/1996 | Greene |
| 5,614,677 A | 3/1997 | Wamsiedler |
| 5,616,375 A | 4/1997 | Mathieu |
| 5,704,756 A | 1/1998 | Marteney et al. |
| 5,730,712 A * | 3/1998 | Falkvall et al. ............ 604/5.01 |
| 5,730,713 A | 3/1998 | Okarma |
| 5,762,805 A | 6/1998 | Truitt |
| 5,776,345 A | 7/1998 | Truitt |
| 5,836,908 A | 11/1998 | Beden |
| 5,846,419 A | 12/1998 | Nederloff |
| 5,858,238 A | 1/1999 | McRea |
| 5,871,694 A | 2/1999 | Beden |
| 5,902,336 A | 5/1999 | Mischkin |
| 5,910,252 A | 6/1999 | Truitt |
| 5,919,369 A | 7/1999 | Ash |
| 6,022,335 A | 2/2000 | Ramaden |

FOREIGN PATENT DOCUMENTS

| | | |
|---|---|---|
| WO | WO98/30258 | 7/1998 |

OTHER PUBLICATIONS

Baldamus et al., *International Society of Nephrology*, pp. S41-S46 (1994).

Quellhorst et al., *Proc. Dialysis Transplant Forum*, pp. 54-58 (1979).

Schaefer et al., *Artificial Organs*, 2(4):386-394.

Quellhorst et al., Long-Term Morbidity: Hemofiltration vs. hemodialysis, Dialysis Membranes: Structure and Predictions Contrib Nephrol. Basel, Karger, 1995, vol. 13, pp. 110-119.

Collins et al., *Kidney Int Suppl*, Dec. 1985, 17:S18-22.

Manns et al., *Kidney International*, vol. 54, 1998, pp. 268-274.

Weiss et al., *Scand J. Urol. Nephrol*, 23(3):223-229 (1989).

Prisma System Operator's Manual, Feb. 1997.

* cited by examiner

HEMOFILTRATION SYSTEM

This is a division of U.S. application Ser. No. 08/800,881, filed Feb. 14, 1997, incorporated herein by reference in its entirety, and which is currently abandoned.

FIELD OF THE INVENTION

The present invention relates generally to a man-made apparatus that substitutes for natural kidney function, and more particularly to a compact, easy-to-use hemofiltration system equipped to maintain accurate net fluid volume change in a patient, and designed and constructed to be usable repeatedly in a patient's home.

BACKGROUND OF THE INVENTION

Loss of human renal function, for example due to kidney disease, affects hundreds of thousands of people worldwide. In the past, chronic renal failure has meant almost certain death. More recently, renal failure is treatable by kidney transplant and/or less-physiologically traumatic procedures such as hemodialysis or hemofiltration. Existing hemodialysis and hemofiltration systems operate by continuously withdrawing blood from a patient, treating the blood to remove waste, and continuously re-introducing treated blood into the patient. Hemodialysis operates by bringing blood into contact with one side of a semi-permeable membrane while a dialysis solution (dialysate) is brought into contact with the other side of the membrane. Uremic toxins diffuse out of the blood, through the semi-permeable membrane due to the concentration gradient across the membrane, and into the dialysate. Hemofiltration operates by passing the blood through a filter to remove waste.

Most man-made renal function systems are not designed for convenient home use. In general, artificial renal treatment is given in a clinical outpatient setting for reasons of safety, since factors such as balance in withdrawn blood and re-introduced replacement fluids are critical. Of course, loss of a threshold amount of blood results in death. However, since victims of renal failure treated by man-made renal function systems must spend a significant amount of time undergoing hemofiltration or hemodialysis, these patients must spend a significant amount of time out of their homes if treated in a clinical setting.

Accordingly, there is a need in the art for high-volume, convenient, and accurate hemofiltration systems that allow for safe and easy home use.

SUMMARY OF THE INVENTION

The present invention provides a set of techniques and systems for providing treatment to patients in need of renal therapy. In one aspect, the invention involves a method of clearing a patient's blood of uremic toxins. The method involves subjecting a patient in need of renal therapy to a protocol involving continuously removing blood from a patient at a blood flow rate of at least 300 ml/min, at least partially clearing the blood of uremic toxins to create cleared blood, and continuously returning the cleared blood to the patient. The protocol is repeated at least four times in one week. The protocol can be repeated five times, six times, or seven times in one week according to various embodiments, and any of these embodiments can be repeated for two weeks, three weeks, one month, two months, or an extended period of time. Typically, these treatments will be repeated 4–7 times per week for many years. The method can be facilitated by one aspect of the invention in which the protocol involves renal therapy at a blood flow rate of at least 400 ml/min. The flow rate can be 500 ml/min, 600 ml/min, or 700 ml/min according to another set of embodiments, and any member of this set of embodiments can be combined with any of the above and other embodiments. For example, the method can involve subjecting a patient in need of renal therapy to blood treatment at a flow rate of at least 300 ml/min at least four times per week, or, for example, at least 600 ml/min at least six times per week. The method can involve accessing a patient's vascular systems through a subcutaneous port, removing the blood from the patient, at least partially clearing the blood, and returning cleared blood to the patient, optionally via the same or a different subcutaneous port.

The methods and systems of the invention facilitate very high clearance rate treatment. One embodiment involves clearing a patient's blood of uremic toxins via hemofiltration at an effective clearance rate of at least 100 ml/min, preferably at least 200 ml/min.

The systems and methods of the invention allow for maintenance of a uremic toxin level in a patient within a convenience and comfort range. That is, because the invention provides a system for convenient in-home hemofiltration therapy, a protocol is facilitated in which a patient's uremic toxins are allowed to reach no more than about 80% of the maximum level compared to thrice-weekly therapy levels, following which the patient's blood is treated to reduce toxins and treatment continues only so long as the blood toxin level is at least 20% of the maximum level compared to thrice-weekly therapy levels. The protocol is repeated at least four times in one week.

The invention also provides a self-contained system for clearing a patient's blood of uremic toxins. The system includes a filter having a first side fluidly connectable to a source of a patient's blood and a second side fluidly connectable to a waste receptacle. A reservoir is provided that contains from about four to about 25 liters of infusate, and the reservoir is fluidly connectable to the patient's blood stream. The infusate reservoir can contain from about 4 to about 18 liters, or from about 9 to about 13, or 10 to about 12 liters in preferred, single day embodiments.

In another embodiment, the invention provides a system for clearing a patient's blood of uremic toxins, including a filter having a first side and a second side, an input conduit in fluid communication with the first side of the filter and fluidly connectable to a patient's blood stream, a return conduit in fluid communication with the first side of the filter for returning cleared blood to the patient's blood stream, a waste receptacle, a waste conduit fluidly connecting the waste receptacle to the second side of the filter, a reservoir containing from about 4 to about 25 liters of infusate, and an infusate conduit fluidly connecting the reservoir to the return conduit. The invention also provides a system including a peristaltic pump, and a fluid conduit passing through the pump and having a portion upstream of the pump. The system includes a valve in the portion of the fluid conduit upstream of the pump.

Also provided in accordance with the invention is a method including adjusting the rate of fluid flow through a peristaltic pump by adjusting the resistance to fluid flow upstream of the pump.

The invention also provides a method including establishing a flow of fluid through a peristaltic pump from a source of the fluid, and changing the rate of flow of the fluid through the peristaltic pump while the pump operates at a constant speed and the source of fluid remains constant. The invention also provides a method including controlling an amount of a replacement fluid added from a reservoir to a blood stream of a patient in response to a signal generated from comparison of (a) a total amount of unaccumulated waste product removed from the blood stream and the replacement fluid in the reservoir with (b) one of the amount of the accumulated waste product and the replacement fluid in the reservoir.

The invention also provides a system including a blood treatment device having an input fluidly connectable to a source of blood drawn from a patient in need of renal treatment, and an output fluidly connectable to a receptacle of blood waste product. The system includes a first scale adapted to determine a first value that is a total amount of the content of the receptacle of blood waste product plus an amount of blood replacement fluid (infusate) in a reservoir. A second scale is provided that is adapted to determine a second value that is at least one of the content of the receptacle of blood waste product or the amount of blood replacement fluid in the reservoir. A microprocessor is provided that is capable of generating a signal indicative of a comparison of the first value and the second value, and a controller is included that is capable of controlling delivery of blood replacement fluid to the patient's blood stream in response to the signal.

The invention also provides a method including urging simultaneously the flow of first and second physiological fluids within first and second conduits, respectively, via actuation of a single fluid pump actuator. The fluid pump can be a peristaltic pump.

The invention also provides a fluid pump. The pump is constructed and arranged for use with a blood treatment system. The treatment system includes a blood treatment device, a withdrawal conduit arranged to supply a source of blood from a patient in need of renal treatment the treatment device, a return conduit arranged to return treated blood from the treatment device to the patient, a waste product conduit arranged to deliver waste product removed from the blood by the treatment device to a waste outlet, and a replacement fluid conduit arranged to deliver a replacement fluid to the patient. The fluid pump is constructed and arranged to urge fluid to flow within at least two of the withdrawal conduit, the return conduit, the waste product conduit, and the replacement fluid conduit. Preferably, the fluid pump is constructed and arranged to urge fluid to flow through the withdrawal conduit, the waste product conduit, and the infusate (replacement fluid) conduit.

The invention also provides an assembly for use with a blood treatment system. The assembly is removably attachable to the system, and includes a blood filter housing having an inlet, a first outlet, and a second outlet. The assembly includes a pump member having a surface that mates with a pump in the treatment system when the assembly is attached to the treatment system. A withdrawal conduit is provided that is in fluid communication with the filter housing inlet and fluidly connectable to a source of blood from a patient in need of renal treatment. A return conduit is provided in fluid communication with the first filter housing outlet and is fluidly connectable to a conduit for returning the treated blood to the patient. A waste product conduit is provided in fluid communication with the second filter housing outlet. At least two of the withdrawal conduit, the return conduit and the waste product conduit are arranged proximate the pump member surface such that, when the assemble is attached to the treatment system, the at least two conduits are actuable by the pump.

The invention also provides a system including a conduit fluidly connectable to a patient's vascular system, and an ultrasonic sensor responsive to fluid flow in the conduit. The sensor includes an output for delivering a signal indicative of fluid flow rate in the conduit. An alarm can be provided, responsive to the signal, that is activated when fluid flow strays outside a predetermined range, and in particular when the fluid flow drops below a predetermined level.

The invention also provide a system for clearing a patient's blood of uremic toxins. The system includes a subcutaneous port providing fluid communication with a patient's vascular system, a filter having a first side and a second side, an input conduit in fluid communication with the first side of the filter and fluidly connectable to the subcutaneous port, a return conduit in fluid communication with the first side of the filter for returning cleared blood to the patient's blood stream, a waste receptacle, a waste conduit fluidly connecting the waste receptacle to the second side of the filter, a reservoir containing from about 4 to about 25 liters of infusate, and an infusate conduct fluidly connecting the reservoir to the return conduit. The system is constructed and arranged to continuously clear the blood of uremic toxins to create cleared blood at a blood flow rate of at least 300 ml/min.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure.

DETAILED DESCRIPTION OF THE INVENTION

The present invention provides a system for the treatment of blood in patients requiring renal therapy, for example in patients suffering renal failure. The system is constructed to be simple to operate safely in the home and allows for the possibility of safe and convenient daily hemofiltration treatments. The hemofiltration therapy facilitated by the system involves passing blood drawn from a patient through a filter to remove uremic toxins (waste material that is removed physiologically by a healthy kidney), and subsequent re-infusion of the blood into the patient. An infusate, or replacement fluid, is added to the blood returned to the patient to at least in part make up for the amount of fluid removed during the filtration process. Typically, fluid will be replaced in an amount slightly less than that removed to decrease the overall fluid level in the patient.

A discussion of the state of the art of hemodialysis and hemofiltration systems and of certain factors and parameters recognized by the inventors of the present invention, will facilitate a better understanding of the implications of the invention. Hemodialysis involves establishment of a flow of a patient's blood along a first side of a semi-permeable membrane in a first direction, and establishment of a dialysate solution flowing typically in the opposite direction on the opposite side of the membrane. The dialysate has a low concentration (typically zero, initially of toxins desirably removed from blood, and a concentration gradient of toxin is established across the semi-permeable membrane causing toxins to diffuse across the membrane out of the blood. The process is limited, ultimately, by the rate of diffusion of toxins across the semi-permeable membrane, so maintaining a very low concentration of toxins on the dialysate side of the membrane is the most effective means of increasing the blood treatment rate. To do this, however, requires large quantities of dialysate, typically provided conveniently only in a clinical setting. Current clinical hemodialysis protocols require approximately 60–120 liters of dialysate per treatment, an amount not conveniently delivered to the home, and perhaps not safely, and conveniently prepared by most potential users in the home. While U.S. Pat. No. 5,484,397 (Twardowski) describes a hemodialysis system for home use, the system requires synthesis, in the home, of dialysis solution from dry chemicals, concentrates, and a large volume of relatively pure water (that is purified in the home).

Since concentration-gradient-driven diffusion of toxins across a membrane is the primary rate limiting factor in dialysis, treatment rate does not increase significantly as blood flow rate adjacent the membrane increases above a certain point. As illustrated in curve A of FIG. 1 (representative of hemodialysis), with increasing blood flow rate adjacent a membrane in a dialysis process, treatment rate increase sharply just above zero flow, but quickly tapers off, that is, diminishes in rate of increase until it reaches an approximate plateau in which any increase in blood flow rate results in very little resultant increase in blood treatment rate.

Figure 1:
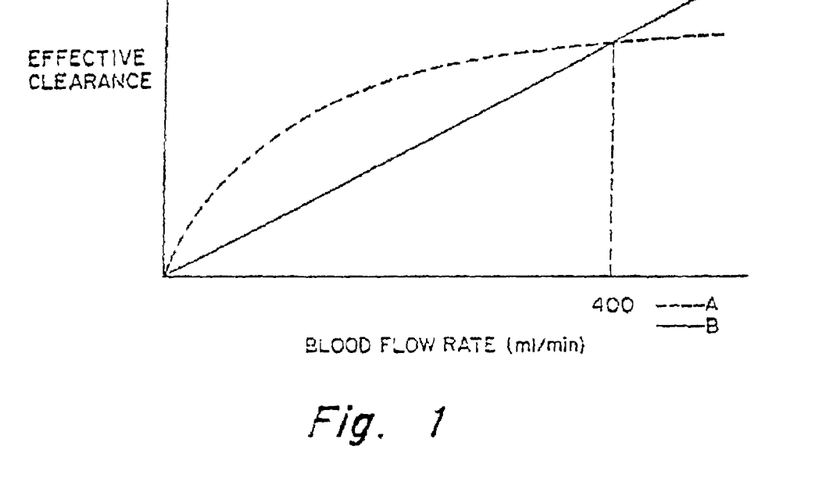
FIG. 1 is an estimated plot of effective blood clearance (treatment rate) versus blood flow rate for hemodialysis (curve A) and hemofiltration (curve B) systems.

In hemofiltration, on the other hand, achievement of acceptably high treatment rates has been determined to be dependent upon blood flow rate. Hemofiltration involves convection of toxins across a membrane, specifically, passage of blood through an ultrafiltration membrane that passes toxins but that restricts the passage of blood cells and other components desirably returned to the patient. The toxins are routed to a waste receptacle, and the blood cells and other components trapped by the filter are returned to the patient's blood stream. Unlike in hemodialysis, in hemofiltration the rate of blood treatment is independent of any concentration gradient across the filter, and instead is dependent upon the rate of clearance of the filter, that is, the rate at which blood cells and other filtrate can be removed from the filter and re-introduced into the patient's bloodstream. The clearance rate is, in turn, dependent only upon the flow rate of the patient's blood through the filter. Therefore, as indicated by curve B of FIG. 1 (representative of hemofiltration), as blood flow rate increases in hemofiltration, blood treatment rate increases significantly, especially at particularly high blood flow rates. Moreover, the 60–120 liters of auxiliary fluid, required in hemodialysis (the dialysate), is not required in hemofiltration. A flow rate of 400 ml/min is suggested as that at which hemodialysis, with state of the art membrane surface areas, and hemofiltration exhibit similar blood treatment rates (effective clearance rate) at similar blood flow rate. FIG. 1 is representative of generalized trends, and is not intended to be precise.

Repeatable, high blood flow rates are not, however, readily achievable. A percutaneous blood flow rate of 420 typically is achievable with a 15 gauge needle through a graft (a subcutaneous polytetrafluoroethylene tube connecting an artery and a vein and serving as a location for access to the vascular system), and a flow rate of 500 can be achieved with a 14 gauge needle through a graft. Access to a patient's vascular system in this manner typically cannot be repeated indefinitely with regularity. Repeated access to a patient's vascular system via a 15 or 14 gauge needle is problematic, and can seriously impact the life of a graft. Needles of this type can "core" grafts, that is, can cut out a portion of a graft.

Figure 2:
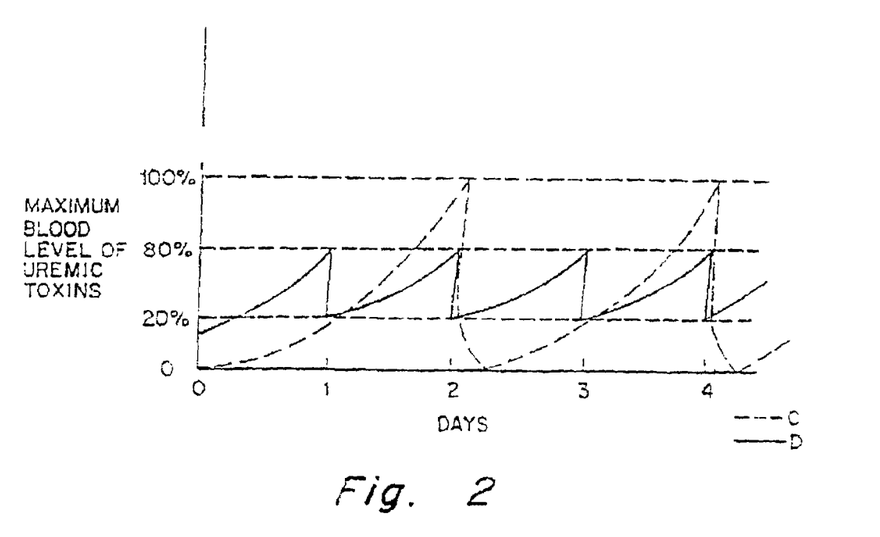
FIG. 2 is a suggested plot of blood toxin level versus days in a bi-daily hemodialysis protocol (curve C) and a daily hemofiltration protocol (curve D)

Since hemodialysis typically is carried out in a clinical setting, most patients select a treatment protocol that does not require daily visits, but only requires treatment every other day. However, as the frequency of treatment drops, the effectiveness of each treatment must be greater. FIG. 2, curve C, is a representative plot of a bi-daily patient treatment protocol. FIG. 2 does not represent actual experiments. On day zero, a patient has just undergone renal therapy, and the patient's blood is clear of uremic toxins. Gradually, over the course of the next two days, the level of uremic toxins in the blood increases until treatment at day two. At day two, just prior to treatment, the level of uremic toxins in the patient's blood has reached maximum tolerable level, that is, the maximum level tolerable without extreme discomfort. This level of toxin is generally unhealthy. For the patient to be able to be free of treatment for the next two days, his blood must be cleared of toxins to the greatest extent feasible, and that level is represented by toxin level 0 in FIG. 2. Hemodialysis relatively rapidly can bring the patient's toxin level from 100% down to 80% and even 20%, but because hemodialysis (unlike hemofiltration) relies for effectiveness on toxin concentration gradient across a membrane, as blood toxin level decreases, toxin removal slows considerably. The final portion of treatment, in which toxin level is decreased from 20% to 0, requires a significant amount of time. Yet that time must be spent unless the patient is willing to return to the clinic for treatment every day, which most patients, given the choice, will not do. In summary, hemodialysis in the outpatient clinic setting typically involves treatment every other day, with some discomfort experienced in the hours just before treatment because of relatively high toxin levels, and significant treatment time is required to achieve the very low toxin levels required to avoid the requirement of treatment every day.

Thus, the invention involves identification of hemofiltration as a much more advantageous treatment technique than hemodialysis, assuming greater accessible blood flow rate. Hemofiltration would be especially effective for home therapy (if the technique could be made feasible for use in the home) since the only auxiliary fluid required in hemofiltration is the infusate. Infusate is added only to partially replace waste removed from blood, and is required only in an amount of about 8–10 liters per treatment. Treatment in the home would result in a treatment protocol that, for most patients, would be tolerable on a daily basis. If a treatment protocol could be carried out on a daily basis, then a blood toxin situation such as curve D would result. In curve D toxin level is maintained at a level no greater than 80% maximum tolerable level, and need not be driven below level 20%. The patient's blood toxin level increases only to a moderate level (80%) after one day, and treatment need be carried out only to the extent necessary to drive the toxin level to the 20% level, since over the next day the toxin level will rise only to 80%. This is advantageous since extra time and effort required for blood clearance to level 0 is not necessary, and the patient need not experience discomfort associated with toxin levels above 80%. In short, since treatment can be carried out conveniently in the home (since 60–120 liters of dialysate is not required), the patient is typically willing to experience treatment every day, and as a result, in combination with high flow rates provided by the invention, the requisite treatment times are quite short, making daily treatment even more tolerable. Although the data plotted in FIG. 2 is not based on actual experiments, the curves of FIG. 2 are representative in that bi-daily hemodialysis or hemofiltration typically requires treatment times of about 4 hours, and daily hemofiltration treatments (provided in accordance with the invention, described in greater detail below) require only about 1.5 hours. Of course, hemodialysis that is carried out in a clinic also requires travel time, set-up, take-down, and other miscellaneous activities that can bring the total time to six hours. Thus not only is treatment carried out safely and conveniently in the comfort of home, according to the in-home daily hemofiltration technique of the invention, but time is saved overall.

The present invention solves, according to one aspect, the problem associated with high treatment rates for hemofiltration, namely low blood flow rate, by providing a high-flow-rate access port. The port makes feasible hemofiltration at rates that reduce treatment times to those tolerable by patients on a daily basis, and the invention also provides a series of hemofiltration systems for safe, convenient, disposable home use. The high-flow-rate port of the invention allows for safe, repeatable, reliable access to a patient's vascular system at flow rates of up to 600–700 ml/min. The port is described in detail in co-pending, commonly-owned U.S. patent application of Burbank, et al., entitled "Valve Port and Method for Vascular Access", filed Jan. 21, 1997 and incorporated herein by reference. High flow rate can be facilitated, also, using a "T" apparatus described in co-pending, commonly-owned, U.S. patent application Ser. No. 08/724,948, filed Nov. 20, 1996 by Finch, et al., entitled "Subcutaneously-Implanted Cannula and Method for Arterial Access", incorporated herein by reference. The port referring to FIG. 3) facilitates high volume withdrawal and/or return of blood to a patient undergoing extracorporeal blood therapy including hemodialysis, hemofiltration, hemodiafiltration, and the like. The port is implantable subcutaneously and can be accessed by passing a needle through a patient's skin (percutaneously) and into the port. Port device 110 includes an upper shell 118, a base plate 120, an internal cylinder 122, and a vertically reciprocating actuator block 124 disposed within the cylinder 122. A spring 126 urges the actuator block 124 upwardly relative to the cylinder 122. When the actuator block 124 is in its upward position, a conduit 114 (passing into a vein or artery) is pinched closed between an upper lip 128 which is a portion of the wall of cylinder 122 and a lower lip 130 which is a portion of the actuator block 124. Proximal end of the conduit 114 is connected to the lower end of a tube 132 which depends into an interior volume of the actuator block 124. The depending tube 132 provides an axial bore 134 for receiving a needle. A needle is introduced through an opening 136 at the upper end of the axial bore 134.

Figure 3:
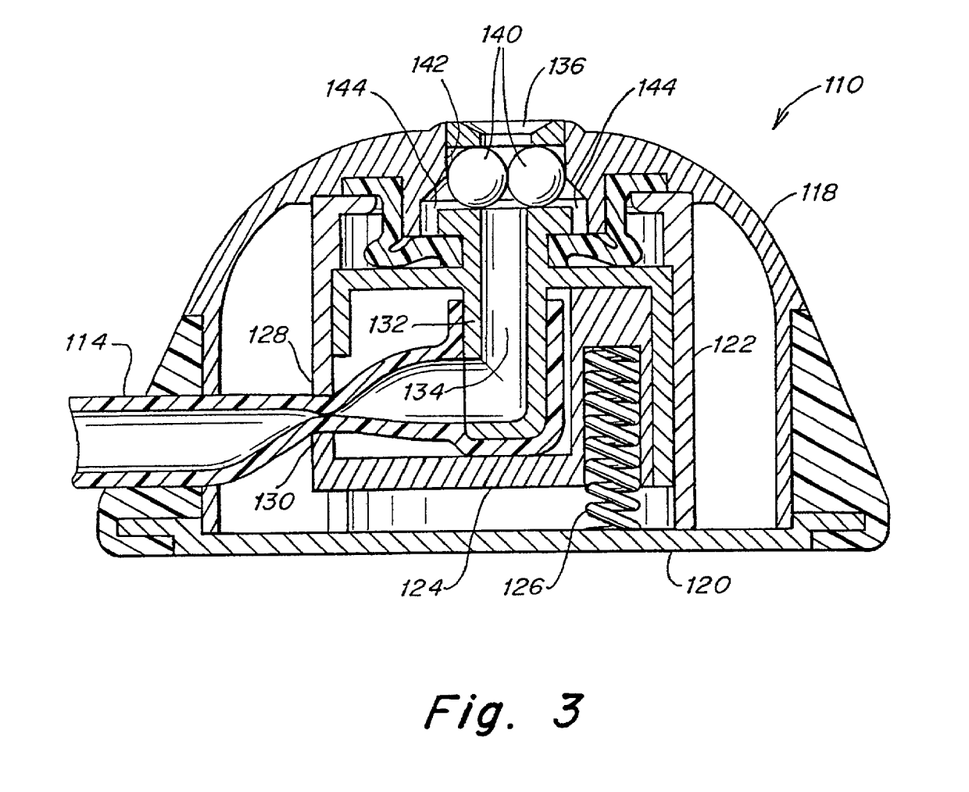
FIG. 3 is a schematic illustration of a high flow rate, subcutaneous vascular access port.

A pair of balls 140 are disposed in an upper portion of the tube 132 and contained within a circular aperture 142 in the shell 118 on the actuator block 124 as in its raised configuration. When a needle is introduced through opening 136, it exerts a force on the balls 140 thereby depressing the actuator block 124 downward until the block reaches a lower configuration, causing opposed lips 128 and 132 to open and thereby fluidly connecting conduits 114 and 132. When the needle is inserted, the balls 140 move radially outwardly into an expanded portion 144 of the aperture 142, and thus become locked within the expanded region so long as the needle remains in place.

The high flow rate access port allows for blood flow rates of at least 300 ml/min, preferably at least 400 ml/min. more preferably at least 420 ml/min. Blood flow rates of at least 500 ml/min. at least 600 ml/min. and even at least 700 ml/min are achievable with the high flow rate access port. The port can be used in conjunction with other components of the invention to provide an overall arrangement that is easy to use by most renal failure patients, is reliable, can be manufactured at relatively low cost, and includes low cost ancillary and disposable apparatus. The setup of the apparatus is very simple. Integrated, pre-primed disposable components clip into place in an intuitive fashion. In a preferred arrangement, a reusable unit is provided, and a disposable assembly including a waste receptacle, infusate reservoir, filter, and various conduits is provided that can be connected to the reusable unit by connection of only two conduit connectors. The reusable unit is pre-primed such that connection at the two connectors, followed by actuation of the reusable unit control processor initiates treatment. The system is constructed such that the unit can be actuated by the user by pressing just one button. Assembly and operation of the device is very straightforward relative to state-of-the-art units.

In connection with hemofiltration systems, arrangements are known for weighing removed waste and weighing fluid infused to replace removed waste to maintain a predetermined fluid level in a patient. Systems are known also for weighing and comparing fresh and spent dialysate in hemodialysis. U.S. Pat. Nos. 4,204,957, 5,344,568, 4,728,433, and 4,132,644 can be consulted for discussions of these systems. Many of the systems, however, lack accuracy and/or precision over the relatively wide weight range in which they are required to operate. In one set of embodiments, the system of the invention includes a scale or set of scales adapted to determine the amount of waste product removed from blood, the amount of replacement fluid (infusate) in a replacement fluid reservoir, and/or both, for monitoring the progress of a treatment and/or for accurately controlling the net amount of fluid removed from the patient during the treatment (or added, although this is rarely indicated in a treatment protocol).

Figure 4:
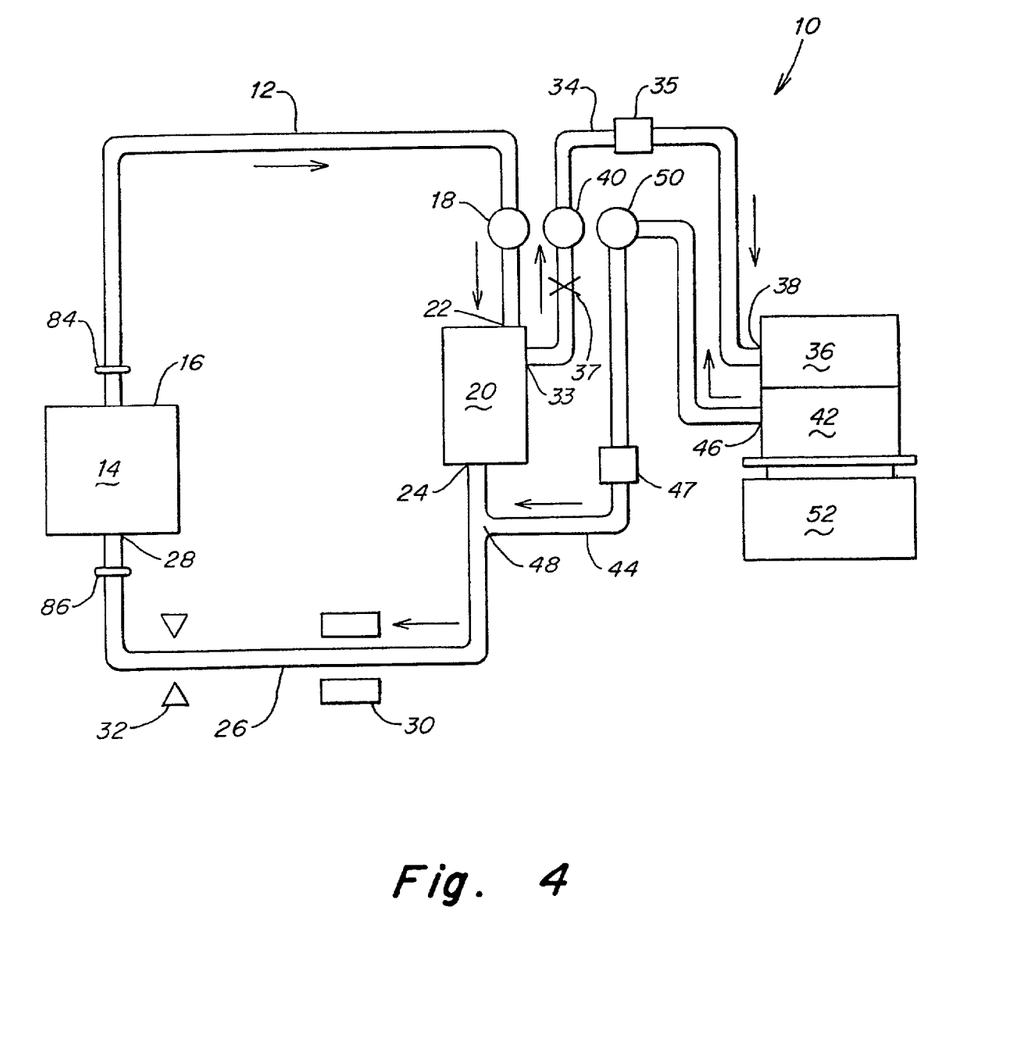
FIG. 4 is a schematic illustration of a hemofiltration system of the invention.

FIG. 4 is a schematic illustration of a blood treatment system 10 in accordance with the invention. The arrangement of FIG. 4 facilitates a method for clearing a patient's blood of toxins by providing a protocol involving removing blood from the patient at a rate of at least 300 ml/min, at least partially clearing the blood of uremic toxins to create cleared blood, and returning the cleared blood to the patient. The protocol can be carried out at least four times per week. A patient blood withdrawal conduit 12 is connected to the vascular system of a patient 14 at a location 16 which, in preferred embodiments, is high-flow rate valve port 110. Blood withdrawal conduit 12 is routed through a pump 18 and supplies blood to a blood treatment unit 20 via an inlet port 22. In preferred embodiments, blood treatment unit 20 is a hemofilter. Treated blood, from which waste product has been removed be system 20, exits treatment unit 20 at outlet 24 and is delivered, via conduit 26, to the vascular system of patient 14 preferably by way of location 28 which, in preferred embodiments, is a high-flow rate port 110. An ultrasonic detector 30 can be provided along line 26 between blood purification system 20 and patient 14 to detect any or all of flow rate, air bubbles (foam), and hematocrit. A safety clamp 32 can be provided as well to stop flow if detector 30 indicates the presence of unacceptable levels of air bubbles. Ultrasonic detector 30 and safety clamp 32 can be operably and electronically linked to the treatment controller, described below.

Waste product (waste filtrate in a hemofiltration system) exits unit 20 via port 33 and passes through conduit 34 via an inlet 38 into a waste product receptacle 36. Conduit 34 passes through a pump 40. A blood detector 35 can be positioned alone conduit 34 to detect any leaks in a filter within blood treatment system 20. The detector detects red blood cells which, if a filter rupture has occurred, will leak into waste line 34, rather than being returned to patient 14. The detector can be controlled by the treatment controller, and operably and electronically linked to a system that stops treatment. An articulated clamp 37 can be positioned along conduit 34 to control, or at least fine tune, the rate of flow through pump 40. This arrangement is described in greater detail below.

A reservoir 42 of a blood replacement fluid, or infusate, is fluidly connected to return conduit 26 via a replacement fluid conduit 44 connecting an outlet 46 of reservoir 42 with a connection 48 between conduit 44 and conduit 26. Conduit 44 passes through a pump 50. Reservoir 42 need include only that amount of infusate required for a particular treatment. Where a bi-daily (every other day) protocol is indicated, infusate reservoir 42 contains from about 8 to about 24 liters of infusate. Where a daily protocol is indicated, reservoir 42 will contain from about 8 to about 12 liters of infusate. As described below, the infusate reservoir can be sold as a pre-packaged, disposable container including a measured amount of infusate for one treatment. The invention provides a system useful for daily hemofiltration, thus reservoir 42 preferably is packaged containing from about 8 to about 12 liters infusate.

A sterile filter 47 is positioned in line 44 between pump 50 and line 26.

Pumps 18, 40, and 50 are peristaltic pumps according to preferred embodiments. This is described in more detail below.

In the embodiment illustrated in FIG. 4, waste receptacle 36 and blood replacement reservoir 42 each rest upon a scale 52. In this arrangement, a net change in patient vascular system fluid content can be determined and thereby controlled. Since waste removed from the patient is registered as an increase in weight on scale 52, and replacement fluid introduced into the patient is registered as a decrease in weight on scale 52, the change in readout of scale 52 is equal to the change in net fluid level within the patient as a result of the treatment.

Figure 5:
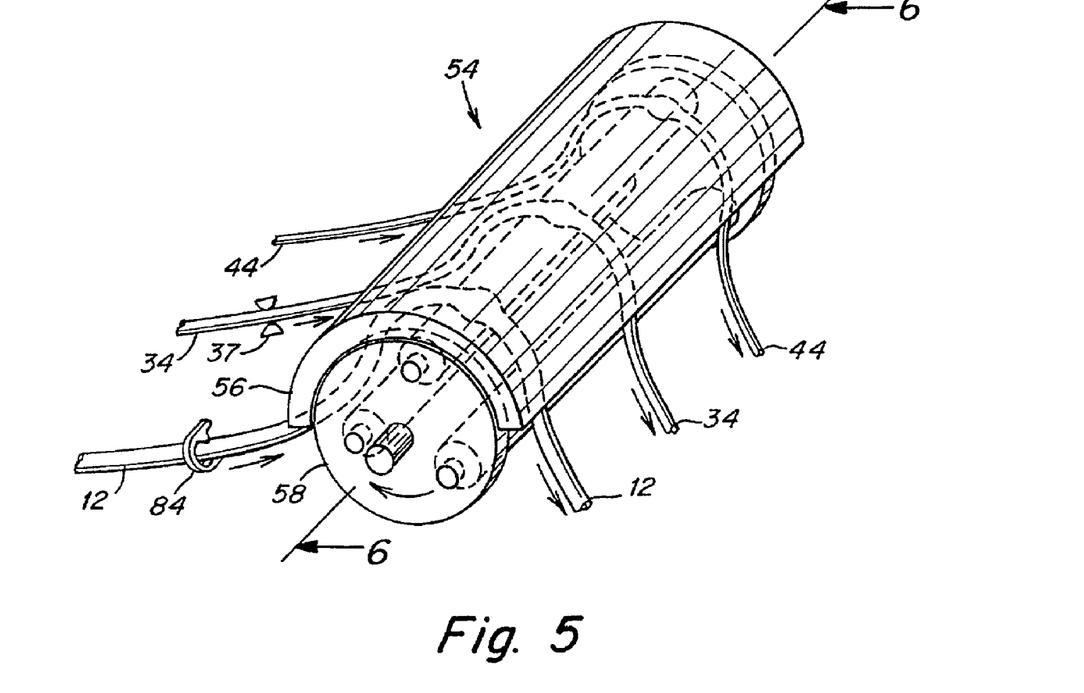
FIG. 5 is a schematic illustration of a pump arrangement of the invention.
Figure 6:
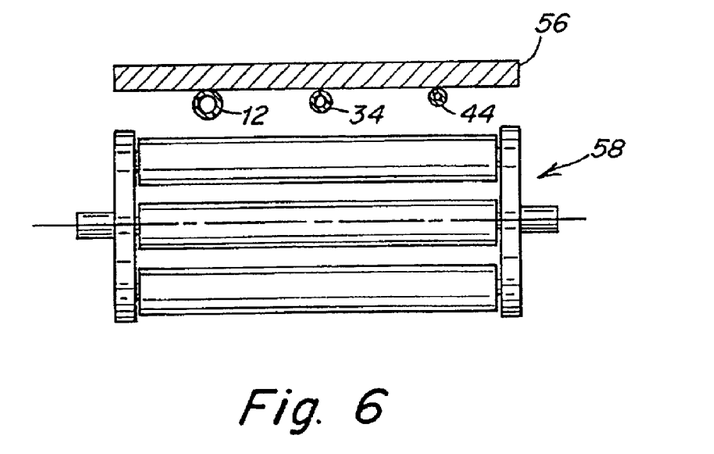
FIG. 6 is a partial cross-sectional view through lines 6—6 of FIG. 5.

In a preferred embodiment of the invention, the pump requirements of at least two of pumps 18, 40, and 50 are met by a single peristaltic pump, and in a particularly preferred embodiment all three of pumps 18, 40, and 50 are one and the same. Peristaltic pumps are known for use with fluids other than physiological fluids, and are commercially available (for example, multi-channel pump 13-874-600, available from Fisher Scientific). This arrangement is illustrated in FIG. 5, which shows a pump 54 (defining all of pumps 18, 40, and 50 of FIG. 4 in preferred embodiments) including a pump race 56 and roller mechanism 58, between which each of blood withdrawal conduit 12, waste removal conduit 34, and blood replacement fluid conduit 44 pass. The arrangement of FIG. 5 allows for establishment of a flow of fluid through the peristaltic pump and changing the rate of flow of the fluid through the pump while the pump operates at a constant speed and the source of fluid supplied to the pump remains constant. That is, a constant source of fluid exits upstream of clamp 37, and the rate of flow of fluid through the pump is changed, by closing clamp 37, while the pump operates at a constant speed. When roller mechanism 58 rotates in a clockwise direction, as illustrated, fluid in each of conduits 12, 34, and 44 is driven in the direction indicated by the arrows. Since the fluid flow rates in conduits 12, 34, and 44 generally will not be identical, each of conduits 12, 34, and 44 has a cross-sectional dimension at pump 54 selected to provide a different flow rate within the respective conduit at a constant pump operation speed. This is illustrated in greater detail in FIG. 6, which is a cross-section through lines 6—6 of FIG. 5. Conduits 12, 34, and 44 each are illustrated in cross-section against interior surface 60 of pump race 56, also shown in cross-section. For purposes of clarity, roller mechanism 58 is shown detached from conduits 12, 34, and 44. The cross-section of conduit 12 is approximately twice the cross-section of conduit 34, which is approximately twice the cross-section of conduit 44 in preferred embodiments, thus, rotation of roller mechanism 58 against pump race surface 60 will cause fluid to flow in conduit 12 at a higher flow rate than within conduit 34, and fluid to flow within conduit 34 at a higher flow rate than within conduit 44. The cross-sections of the various conduits can be adjusted for desired flow rates. Where the tubing wall thickness differs from conduit to conduit, a stepped pump rate can be provided.

For precise control of flow rates within lines 12, 34, and 44, that is, for precise tuning of the flow rates within these lines independent of pump 54, auxiliary clamps can be used, for example articulated clamp 37 (FIG. 4). Articulated clamp 37 is illustrated along line 34 in FIG. 5. When fluid is being driven through lines 12, 34, and 44 simultaneously by pump 54, and is flowing through the lines at different respective rates because of the different cross sections of the lines, fine tuning of the flow rate can be controlled manually, or automatically with a feedback mechanism, with clamp 37. When clamp 37 impinges upon line 34, fluid flow through the clamped conduit is restricted causing pressure drop, thus the cross section of the conduit downstream of the clamp will be reduced slightly due to the negative pressure. Typically, the cross section will be made slightly ovoid due to decrease in fluid volume, thus each rotation of roller mechanism 58 will cause a lesser amount of fluid to flow through that conduit which is slightly clamped upstream of the pump. The peristaltic pump thus includes at least a first and a second conduit each connected to a source of physiological fluid. Preferably, at least three conduits driven by the pump are connected to physiological fluid sources.

Figure 7:
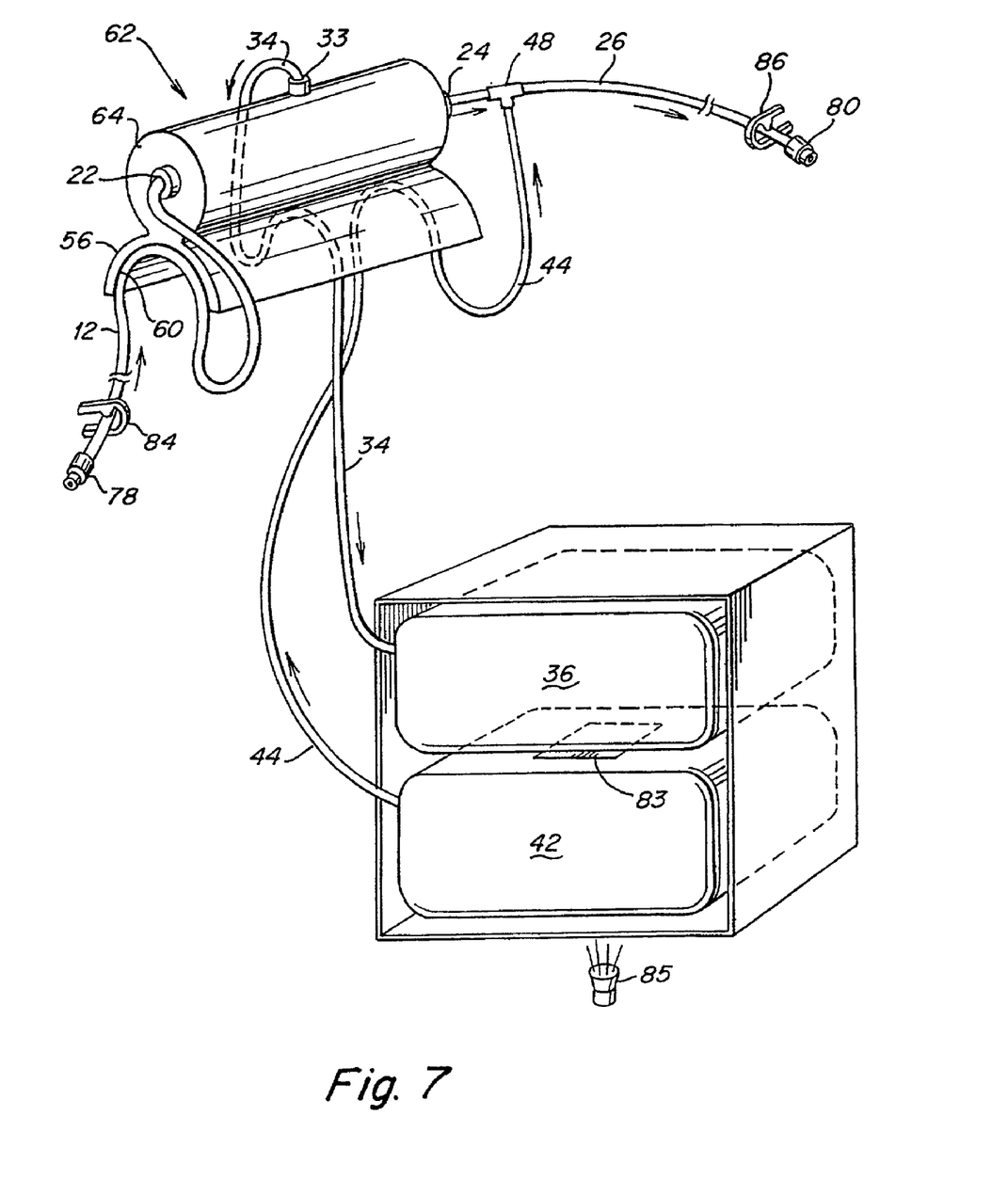
FIG. 7 is a schematic illustration of a pump race, filter housing, replacement fluid reservoir, and waste receptacle in accordance with the invention including a device for sensing the flow of replacement fluid from the reservoir.

Referring now to FIG. 7, any disposable, single use assembly 62 including a filter housing 64 integrally connected to pump race 56, along with waste receptacle 36 and infusate reservoir 42 is illustrated. The assembly is movably attachable to a blood treatment system of the invention in a manner such that when attached, pump race 56 is engaged by roller mechanism 58 driven by the system. In assembly 62, withdrawal conduit 12 is fluidly connected to the filter housing inlet 22 and return conduit 26 is fluidly connected to filter housing outlet 24. Waste product conduit 34 is fluidly connected to another filter housing outlet 33. Withdrawal conduit 12 is fluidly connectable via a connector 78 to the patient's vascular system, i.e., a vein or artery (via the "T" described in application Ser. No. 08/724,948, referenced above). Return conduit 26 is connectable via a connector 80 to the patient's vascular system in the same manner. The connectors 78 and 80 can be connected to a needle or fistula before or after insertion into the patient's vein or artery, optionally via port 110, described above.

Withdrawal conduit 12 and waste conduit 34 are mounted within race 56 such that when assembly 62 is connected to the blood treatment controller, these conduits are engaged by and actuated by roller mechanism 58. In addition, replacement fluid conduit 44 is routed adjacent race surface 60 of race 56 for actuation by roller mechanism 58 when the assembly is attached to the treatment system.

In the embodiment illustrated in FIG. 7, waste receptacle 36 and infusate reservoir 42 are irremovably connected via conduits 34 and 44, respectively, to assembly 62. A reservoir 42 is fluidly connected to return conduit 26 via a replacement fluid conduit 44 connecting an outlet 46 of reservoir 42 with a connector 48 between conduit 44 and conduit 26. In this arrangement, assembly 62, including filter housing 64 and pump race 56, along with waste receptacle 36, infusate reservoir 42, and conduits 12, 26, 34 and 44 all form an integral unit that is disposable. In use, the unit is provided with an empty waste receptacle and provided with replacement fluid in reservoir 42, with lines 44, 34, 26, and 12 optionally being primed. Connection of the arrangements to the patient's vascular system (described in greater detail below) via connectors 78 and 80, respectively, followed by connection pump member (race) 56 to the treatment controller for actuation by roller mechanism 58, and unclamping of clamps 84 and 86, respectively, renders the system ready for use. Following a treatment protocol, the system can be detached and the entire assembly 62, including conduits 12, 26, 24, and 44, filter housing 64 including a filter, pump race 56, and waste receptacle 36 and infusate reservoir 42 can be disposed of.

In the embodiment illustrated in FIG. 7, a reflective foil member 83 is provided to confirm that replacement fluid flow out of reservoir 42 and through conduit 44 is occurring. A light source and detector 85 irradiates reflective foil member 83 for detection. A variety of sensing mechanisms such as optical sensors, ultrasonic sensors, or other sensors can be used to detect replacement fluid flow. Preferably, waste receptacle 36 and infusate reservoir 42 are packaged together in a box, for shipment. When the box arrives in the patient's home, the patient need only place the box on a scale, open a lid or other opening in the box and remove the filter, pump race, and other tubing, remove a sterility barrier from each of connectors 78 and 80, and connect the system to the vascular system as described.

In alternative embodiments, with reference to FIG. 7, any combination, or all, of conduits 12, 44, 34, and 26 can be mounted against race surface 60 of race 56. In preferred embodiments, withdrawal conduit 12, replacement fluid conduit 44, and waste conduit 34 are so mounted. In one embodiment, one or both of conduits 44 and 34 are two-part conduits, the two-parts of each conduit joined with connectors such as connectors 78 and 80. In this arrangement, one or both of waste receptacle 36 and replacement fluid reservoir 42 are reusable, and disconnectable from disposable assembly 62 via a connector. In such an arrangement, an additional clamp is preferably provided on the assembly 62 side of the connector, and the conduit is primed.

Figure 8:
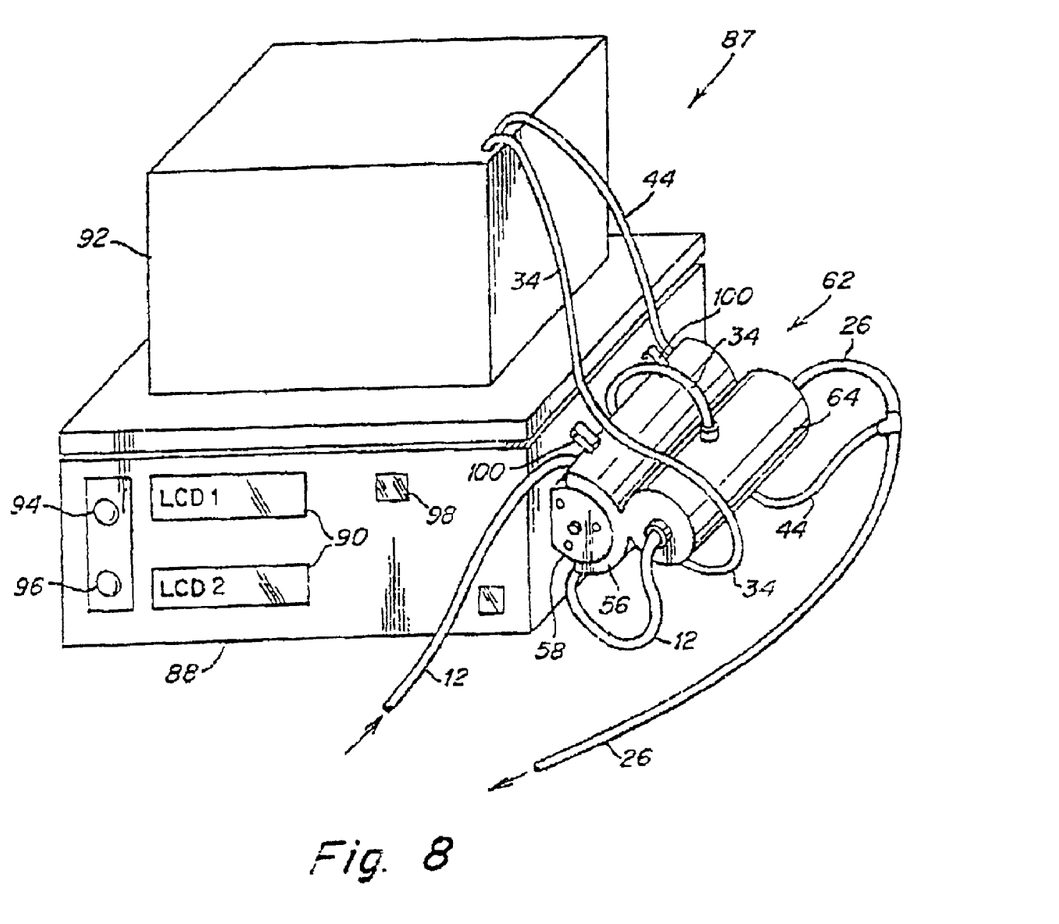
FIG. 8 is a schematic illustration of a blood treatment system of the invention.

Referring now to FIG. 8, a blood treatment system 87 is illustrated including a controller housing 88 containing a microprocessor that controls blood treatment, and that includes one or more displays 90. A two-button device is shown; including a "start" button 94 and a "stop" button 96. An alarm light 98 indicates malfunction.

Housing 88 also contains a scale, the receiving surface 91 of which, as illustrated, supports a container 92 containing waste receptacle 36 and replacement fluid reservoir 42 (not shown). Assembly 62 including filter housing 64, pump member (race) 56, a portion of withdrawal conduit 12, a portion of return conduit 26, replacement fluid conduit 44, and waste fluid conduit 34 is attached to the treatment system via latches 100. When connected in this way, pump roller mechanism 58, which is mounted as an integral part of the blood treatment system, acts to pump fluid through conduits 12, 34, and 44.

In the arrangement illustrated, the microprocessor within housing 88 controls actuation of pump roller mechanism 58 during treatment, and the scale monitors the total weight of the waste receptacle 36 and replacement fluid reservoir 42. The microprocessor typically will be programmed to allow treatment to progress so long as a gradual net weight gain of the waste receptacle and replacement fluid reservoir is observed. This will correspond to a net fluid loss in a patient, which is desirable. If the weight of the combination of the waste receptacle and replacement fluid reservoir strays outside of that range, alarm light 98 will light, indicating malfunction, and the pump will stop. The system can be set such that a weight change outside of a particular set of boundaries will cause the system to shut down.

One way in which the total weight of the waste receptacle and replacement fluid reservoir can stray outside of a predetermined range is if there is a leak in the waste conduit. In this case, were the system to continue to operate, the patient would become infused with excess replacement fluid.

Figure 9:
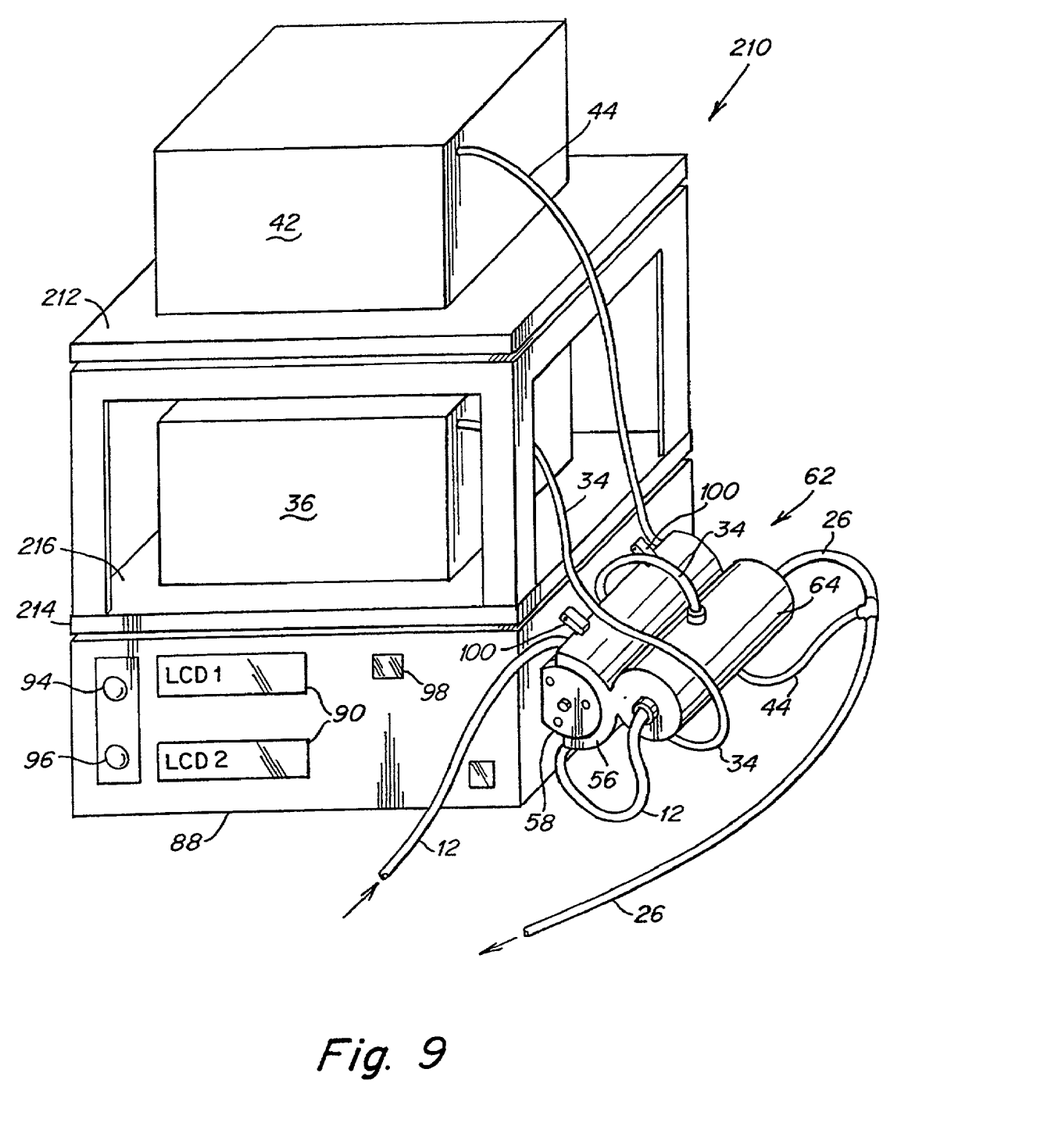
FIG. 9 is a schematic illustration of a blood treatment system according to another embodiment of the invention.

Referring now to FIG. 9, a blood treatment system 210 according to another aspect of the invention is illustrated. In system 210, a first scale 212 is provided along with a second scale 214. Scale 212, as illustrated, rests on a scale surface 216 of scale 214, thus scale 214 registers the weight of waste receptacle 36 and replacement fluid reservoir 42, and scale 212 registers only the weight of replacement fluid reservoir 42. In this manner, as replacement fluid is consumed and waste receptacle 36 is filled, scale 214 will display a net change that equals the difference between replacement fluid consumed and waste product recovered. Scale 212 will display only a change in weight resulting from consumption of replacement fluid. This arrangement is more sensitive than prior art systems involving one scale for determination of weight of waste product and another scale for determination of weight of replacement fluid for the following reasons. In the embodiment illustrated, if 10,000 grams of replacement fluid exists initially in reservoir 42, and all is consumed during the procedure, and the waste receptacle 36 is empty at the beginning of the procedure and contains 11,000 grams waste at the end of the procedure, then scale 212 will record 10,000 grams initially, and zero grams finally, and scale 214 will record 10,000 grams initially and 11,000 grams finally. A scale that is required to operate over a smaller range of weight typically will provide more accurate and precise weight information. Since accurate weight information is important in the blood treatment protocol, it is preferred that the weight range through which scale 214 must record data be minimized. The arrangement of FIG. 9 provides this minimization of required range of scale readout. In one aspect of the arrangement of FIG. 9 that is particularly preferred, scale 214, which records 300 grams initially and 500 grams finally, operates over a range of only 200 grams. This allows greater precision in scale 214, and precision is particularly important in measuring the net change in fluid content of the patient during treatment. One scale (212) is used only to determine that the infusate is being pumped. A high level of accuracy is not required in this determination.

Referring again to FIG. 4, in combination with FIGS. 5–9, a series of embodiments of the invention that provide for a range in degree of disposability, and that provides for simple operation of the system of the invention in the home, are described. Referring to FIGS. 4 and 7, a system which is essentially completely disposable with the exception of the system controller and scales (described above), involves a disposable filter and filter housing 20, disposable pump race 56, disposable waste receptacle 36 and infusate reservoir 42, and disposable conduits 12, 34, 44, and 26. The system can be entirely pre-primed, with the only required assembly by the user, in the home, involving removal of the described system from a package, and attachment of the system, fluidly, at only two locations (connectors 78 and 80) to a conduit that establishes fluid communication with the vascular system of the patient via needles to port 110. In one set of embodiments, connectors 78 and 80 insert directly into high flow rate access port 110. In another set of embodiments, each of connectors 78 and 80 is fluidly connectable to a fistula set including a needle or other device for insertion into port 110 or to percutaneous catheters. Other than connection of the assembly to the vascular system of the patient via connectors 78 and 80, the filter housing 64/pump race 56 assembly need only be fastened to controller 88 via laches 100, and the controller can be started simply by pushing button 94.

In another arrangement, the filter is reusable (can be regenerated by the user) and can be cleaned between uses, but lines 12, 34, 44, and 26, and the waste receptacle and infusate reservoir are disposable after one use. In this embodiment, the simple two-connector assembly, along with attachment of the filter/pump race assembly to the control unit, requires only the additional insertion of the regenerated filter into the filter housing. The filter housing can have an opening at one end thereof which is removable, allowing the filter to be removed and inserted easily without requirement of any other conduit disconnections or connections. Alternatively, the system can be designed so that the filter can be regenerated while remaining in the filter housing by attachment of regeneration lines to the filter housing and appropriate treatment. Where the filter and filter housing both are removable, conduits 12 and 26 can be removed from the filter housing and disposed, and during the next use new conduits attached.

In another aspect of the invention, a system for removal of uremic toxins from blood is equipped to accurately measure arterial blood pressure without, at any location in the system, a drip chamber. Drip chambers are used to measure blood pressure, but can be disadvantageous since at high flow rates they can infuse bubbles into the flow of blood, which is problematic. Additionally, drip chambers add cost. In the present invention (with reference to FIG. 4), ultrasonic blood flow detector 30 can be used to measure arterial blood pressure as follows. The speed of rotation of peristaltic pump 18 will give an indication of blood flow rate, but this indication may be inaccurate (as is known for peristaltic pumps) due to negative pressure. The flow rate provided by ultrasonic sensor 30 is very accurate, however, and comparison of the actual flow rate from sensor 30 with the indicated flow rate of pump 18, and comparison of the difference between these values, can provide one of ordinary skill in the art with actual pressure in withdrawal conduit 12 which typically is fluidly connected to a patient's artery.

What is claimed is:

1. A method for-extracorporeal blood treatment, comprising the steps of:
   providing a blood treatment machine including at least one pump and a disposable filter; a fluid circuit including a blood withdrawal line, a blood return line, and a waste line being connected to said filter;
   a replacement fluid line connected to said tubing set to dilute blood carried in at least one of said blood return and blood withdrawal lines;
   connecting the patient's vascular system to the blood withdrawal and return lines;
   engaging a single member carrying said waste, replacement fluid, and blood withdrawal lines to a treatment machine;
   the member and treatment machine being configured such that by said step of engaging a single member, said at least one pump is enabled to pump fluid through said waste, withdrawal and return lines;
   withdrawing blood through a blood withdrawal line at a rate of at least 300 ml/mm passing the blood through a filter to remove waste; and
   passing the filtered blood through a blood return line and into the patient, wherein blood is withdrawn from and returned to the patient continuously for about 1.5 hours, and wherein the blood flow rate is at least 400 ml./min.

2. The method of claim 1, wherein an amount of replacement fluid is added to the blood, and wherein the amount id determined by gravimetric balancing of the replacement fluid and the waste.

3. The method of claim 2, wherein the amount of the replacement fluid is approximately 9–13 liters.

4. The method of claim 2, wherein the replacement fluid is added to the blood after filtration.

5. The method of claim 1, wherein the blood withdrawal line, the filter, and the blood return line are pre-attached and disconnectable from said treatment machine.

6. The method of claim 1, further comprising step of repeating the procedure at least daily.

7. The method of claim 1, wherein the procedure is conducted at home.

8. The method of claim 1, further comprising the step of repeating the procedure for more than one week.

9. The method of claim 1, further comprising the steps of connecting the blood withdrawal line to the patient and connecting the blood return line to the patient.

10. the method of claim 9, wherein the blood withdrawal line and the blood return line are connected to the patient through a subcutaneous port.

11. The method of claim 1, wherein the blood withdrawal line and the blood return line are in registry with said at least one pump and said at least one pump includes a peristaltic pump.

12. The method of claim 1, wherein at least one of the blood withdrawal line and the blood return line further comprises a leak detector.

13. A method for hemofiltration, comprising the steps of:
withdrawing blood through a blood withdrawal line at a rate of at least 300ml/min.;
passing the blood through a filter to remove waste;
and passing the filtered blood through a blood return line and into the patient, wherein blood is withdrawn from and returned to the patient continuously for about 1.5 hours, and wherein the blood flow rate is at least 400ml./min;
pumping the withdrawn blood with a pump at a predetermined blood flow rate;
measuring the actual blood flow rate delivered by the pump using a flow sensor;
comparing the actual blood flow rate with a blood flow rate indicated by a pump speed; and
activating an alarm responsively to a difference between the actual blood flow rate indicated by said flow sensor and the blood flow rate indicated by a pump speed such that said alarm is activated when said difference exceeds a predetermined value.

14. A method as in claim 13, further comprising determining a pressure responsively to said difference.

15. A method for-extracorporeal blood treatment, comprising the steps of:

providing a blood treatment machine including at least one pump and a disposable filter; a fluid circuit including a blood withdrawal line, a blood return line, and a waste line being connected to said filter;
a replacement fluid line connected to said tubing set to dilute blood carried in at least one of said blood return and blood withdrawal lines;
connecting the patient's vascular system to the blood withdrawal and return lines;
fastening a member carrying said waste, replacement fluid, and blood withdrawal lines to a treatment machine; the member and treatment machine being configured such that by said step of connecting, said waste, withdrawal, and return lines are engaged by, and actuated by, said pump;
withdrawing blood through a blood withdrawal line at a rate of at least 300 ml/mm passing the blood through a filter to remove waste; and
passing the filtered blood through a blood return line and into the patient, wherein blood is withdrawn from and returned to the patient continuously for about 1.5 hours, and wherein the blood flow rate is at least 400 ml./min.

* * * * *